US010996301B2

(12) United States Patent
Eggers

(10) Patent No.: US 10,996,301 B2
(45) Date of Patent: May 4, 2021

(54) DUAL-ECHO DIXON-TYPE WATER/FAT SEPARATION MR IMAGING

(71) Applicant: KONINKLIJKE PHILIPS N.V., Eindhoven (NL)

(72) Inventor: Holger Eggers, Ellerhoop (DE)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 16/619,558

(22) PCT Filed: Jun. 8, 2018

(86) PCT No.: PCT/EP2018/065175
§ 371 (c)(1),
(2) Date: Dec. 5, 2019

(87) PCT Pub. No.: WO2018/224653
PCT Pub. Date: Dec. 13, 2018

(65) Prior Publication Data

US 2020/0132794 A1 Apr. 30, 2020

(30) Foreign Application Priority Data

Jun. 9, 2017 (EP) .................................... 17175127

(51) Int. Cl.
*G01R 33/48* (2006.01)
*A61B 5/055* (2006.01)
(Continued)

(52) U.S. Cl.
CPC .......... *G01R 33/4828* (2013.01); *A61B 5/055* (2013.01); *G01R 33/3852* (2013.01);
(Continued)

(58) Field of Classification Search
CPC ............ G01R 33/3852; G01R 33/4828; G01R 33/485; G01R 33/5615; G01R 33/56509;
(Continued)

(56) References Cited

U.S. PATENT DOCUMENTS

2004/0222792 A1* 11/2004 St. Pierre ........... G01R 33/5659 324/307
2009/0072826 A1 3/2009 Hargreaves et al.
(Continued)

OTHER PUBLICATIONS

Rahimi et al "Flow Induction Signal Misallocation Artifacts in Two-Point Fat-Water Chemical Shift MRI" Magnetic Resonance in Med. 73: p. 1926-1931 (2015).
(Continued)

*Primary Examiner* — Gregory H Curran

(57) ABSTRACT

The invention relates to a method of Dixon-type MR imaging. It is an object of the invention to provide a method that enables efficient and reliable water/fat separation using bipolar readout magnetic field gradients and avoids flow-induced leaking and swapping artifacts. According to the invention, an object (10) is subjected to an imaging sequence, which comprises at least one excitation RF pulse and switched magnetic field gradients, wherein two echo signals, a first echo signal and a second echo signal, are generated at different echo times (TE1, TE2). The echo signals are acquired from the object (10) using bipolar readout magnetic field gradients. A first single echo image is reconstructed from the first echo signals and a second single echo image is reconstructed from the second echo signals. A zero echo time image is computed by extrapolating the phase of the first single echo image at each voxel position to a zero echo time using the phase difference between the first and the second single echo image at the respective voxel position. Flow-induced phase errors are identified and estimated in the zero echo time image, and the phase of the first
(Continued)

18 17 15 16 2 2' 9 7 8 11 12 13 14 4 5 6 3 10 9 2' 2 1 z x single echo image is corrected according to the estimated flow-induced phase errors. Finally, a water image and/or a fat image are reconstructed from the echo signals, wherein signal contributions from water and fat to the echo signals are separated using the phase-corrected first single echo image and the second single echo image. Moreover, the invention relates to a MR device (1) and to a computer program to be run on a MR device (1).

12 Claims, 2 Drawing Sheets

(51) Int. Cl.

*G01R 33/385* (2006.01)
*G01R 33/485* (2006.01)
*G01R 33/561* (2006.01)
*G01R 33/565* (2006.01)

(52) U.S. Cl.

CPC ....... *G01R 33/485* (2013.01); *G01R 33/5615* (2013.01); *G01R 33/56509* (2013.01); *G01R 33/56518* (2013.01); *G01R 33/56554* (2013.01); *G01R 33/56563* (2013.01)

(58) Field of Classification Search

CPC ........ G01R 33/56518; G01R 33/56554; G01R 33/56563; A61B 5/055

See application file for complete search history.

(56) References Cited

U.S. PATENT DOCUMENTS

2010/0244822 A1 9/2010 Yu et al.
2010/0260397 A1* 10/2010 Block ................ G01R 33/5614 382/131
2011/0014129 A1* 1/2011 Zabow .................. A61K 49/18 424/9.34
2014/0368195 A1 12/2014 Eggers et al.
2015/0061672 A1 3/2015 Kannengiesser et al.
2016/0313421 A1 10/2016 Fuderer
2017/0307715 A1 10/2017 Eggers et al.
2018/0299526 A1 10/2018 Eggers

OTHER PUBLICATIONS

Eggers et al “Dual Echo Dixon Imaging With Flexible Choice of Echo Times” Magnetic Resonance in Med. 65 p. 96-107 (2011).
Lu et al Improved Spectral Selectivity and Reduced Susceptibility in SSFP Using a Near Zero TE Undersampled Three-Dimensional PR Sequence Journal of Magnetic Resonance, vol. 19, No. 1 p. 117-123 (2004).
Berglund et al “Two-Point Dixon Method With Flexible Echo Times” Magnetic Resonance in Med. 65 p. 994-1004 (2011).
Lu et al “Water-Fat Separation With Bipolar Multiecho Sequences” Magnetic Resonance in Med. 60 p. 198-209 (2008).
Search Report From PCT/EP2018/065175 dated Sep. 11, 2018.

* cited by examiner

DUAL-ECHO DIXON-TYPE WATER/FAT SEPARATION MR IMAGING

CROSS REFERENCE TO RELATED APPLICATIONS

This application is a U.S. national phase application of International Application No. PCT/EP2018/065175 filed on Jun. 8, 2018, which claims the benefit of EP Application Serial No. 17175127.4 filed on Jun. 9, 2017 and is incorporated herein by reference.

FIELD OF THE INVENTION

The invention relates to the field of magnetic resonance (MR) imaging. It concerns a method of MR imaging of an object placed in the examination volume of a MR device. The invention also relates to a MR device and to a computer program to be run on a MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field $B_0$ whose direction at the same time defines an axis (normally the z-axis) of the co-ordinate system on which the measurement is based. The magnetic field $B_0$ produces different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view the distribution of the individual nuclear spins produces an overall magnetization which can be deflected out of the state of equilibrium by application of an electromagnetic pulse of appropriate frequency (RF pulse) perpendicular to the z-axis, so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, the spins are deflected from the z-axis to the transverse plane (flip angle 90°).

After termination of the RF pulse, the magnetization relaxes back to the original state of equilibrium, in which the magnetization in the z direction is built up again with a first time constant $T_1$ (spin-lattice or longitudinal relaxation time), and the magnetization in the direction perpendicular to the z direction relaxes with a second time constant $T_2$ (spin-spin or transverse relaxation time). The variation of the magnetization can be detected by means of receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal in the receiving coils.

In order to realize spatial resolution in the body, constant magnetic field gradients extending along the three main axes are superposed on the uniform magnetic field $B_0$, leading to a linear spatial dependency of the spin resonance frequency. The signal picked up in the receiving coils then contains components of different frequencies which can be associated with different locations in the body. The signal data obtained via the receiving coils correspond to the spatial frequency domain and are called k-space data. The k-space data usually include multiple lines acquired with different phase encoding. Each k-space line is digitized by collecting a number of samples. A set of k-space data is converted to an MR image, e.g., by means of Fourier transformation.

In MR imaging, it is often desired to obtain information about the relative contribution of water and fat to the overall signal, either to suppress the contribution of one of them or to separately or jointly analyze the contribution of both of them. These contributions can be calculated if information from two or more corresponding echoes, acquired at different echo times, is combined. This may be considered as chemical shift encoding, in which an additional dimension, the chemical shift dimension, is defined and encoded by acquiring two or more MR images at slightly different echo times. For water/fat separation, these types of experiments are often referred to as Dixon-type of measurements. By means of Dixon MR imaging or Dixon water/fat MR imaging, a water/fat separation is achieved by calculating contributions of water and fat from two or more corresponding echoes, acquired at different echo times. In general such a separation is possible because there is a known precessional frequency difference of hydrogen in fat and water. In its simplest form, water and fat images are generated by either addition or subtraction of the 'in-phase' and 'out-of-phase' datasets.

Several Dixon-type MR imaging methods have been proposed in recent years. Apart from different strategies for the water/fat separation, the known techniques are mainly characterized by the specific number of echoes (or 'points') they acquire and by the constraints that they impose on the used echo times. Conventional so-called two- and three-point methods require in-phase and opposed-phase echo times at which the water and fat signals are parallel and antiparallel in the complex plane, respectively. Three-point methods have gradually been generalized to allow flexible echo times. Thus, they do not restrict the angle or phase between the water and fat signals at the echo times to certain values anymore. In this way, they provide more freedom in imaging sequence design and enable in particular a trade-off between signal-to-noise ratio (SNR) gains from the acquisition and SNR losses in the separation. On the other hand, sampling only two instead of three echoes is desirable to reduce scan time. Eggers et al. (Magn. Reson. Med., 65:96-107, 2011) have proposed a dual-echo flexible Dixon-type MR imaging method. Using such Dixon-type MR imaging methods with flexible echo times, in-phase and opposed-phase images are no longer necessarily acquired, but optionally synthesized from water and fat images.

Flow is known to be a cause of artifacts in Dixon water/fat imaging. These artifacts result when the phase of the MR signal at a given voxel position accrues by moving water molecules and is misinterpreted by the Dixon reconstruction algorithm according to the signal model used, such that a fraction of the MR signal that should appear in the water image is inappropriately allocated to the fat image for voxels that contain the moving water molecules.

Various strategies can be used in Dixon imaging for acquiring echo signals at two different echo times, including: (i) dual-pass strategies, wherein each echo signal is acquired separately after an excitation RF pulse using a positive amplitude readout magnetic field gradient, (ii) fly-back strategies, wherein both echo signals are acquired after the same excitation RF pulse using a positive amplitude readout magnetic field gradient in combination with a negative amplitude re-winder magnetic field gradient, and (iii) bipolar strategies, wherein both echo signals are acquired after the same excitation RF pulse, one echo being acquired using a positive amplitude readout magnetic field gradient and the other echo being acquired using a negative amplitude readout magnetic field gradient.

Bipolar strategies permit good sampling efficiency and allow for relatively long readout times, but they suffer from several phase errors. In particular, bipolar gradients are known to be flow sensitizing because they lead to a phase offset in the MR signals of moving spins proportional to the velocity of the spins in the direction of the readout magnetic field gradient in the first echo, or in general the odd echoes. In Dixon water/fat separation methods, flow-induced phase offsets can be a source for undesired misallocations of signals between fat and water images (see Rahimi et al., Magn. Reson. Med., 73:1926-1931, 2015). It is thus an object of the invention to provide a method that enables efficient and reliable Dixon water/fat separation using bipolar strategies and avoids flow-induced leaking and swapping artifacts.

SUMMARY OF THE INVENTION

In accordance with the invention, a method of MR imaging of an object placed in an examination volume of a MR device is disclosed. The method comprises the following steps:

subjecting the object to an imaging sequence, which comprises at least one excitation RF pulse and switched magnetic field gradients, wherein two echo signals, a first echo signal and a second echo signal, are generated at different echo times, acquiring the echo signals from the object using bipolar readout magnetic field gradients, reconstructing a first single echo image from the first echo signals and a second single echo image from the second echo signals, computing a zero echo time image by extrapolating the phase of the first single echo image at each voxel position to a zero echo time using the phase difference between the first and the second single echo image at the respective voxel position, identifying and estimating flow-induced phase errors in the zero echo time image, correcting the phase of the first single echo image according to the estimated flow-induced phase errors, and reconstructing a water image and/or a fat image from the echo signals, wherein contributions from water and fat to the echo signals are separated using the phase-corrected first single echo image and the second single echo image.

According to the invention, a multi-echo, e.g. dual-echo multi-point Dixon MR imaging is performed, wherein for example a bipolar acquisition strategy is applied. The two echo signals are acquired using a pair of temporally adjoining readout magnetic field gradients having opposed polarities. The first echo is acquired at a first echo time using a positive amplitude readout magnetic field gradient and the second echo is acquired at a second echo time using a negative amplitude readout magnetic field gradient (or vice versa). The invention may also be employed in conjunction with other read-out approaches to acquire echo signals at different echo times. Different sub-sequences, with respective different echo times may be employed to subsequently acquired the echo signals at different echo times. For example, echoes of different echo times may be acquired in sub-sequences, each having a different echo times. Different echo time may also be obtained in spin echo trains or gradient echo trains.

Single echo images are reconstructed from the acquired echo signals. The first single echo image is reconstructed from the first echo signals attributed to the first echo time value, and the second single echo image is reconstructed from the second echo signals attributed to the second echo time value. The two single echo images are the basis of the water/fat separation to reconstruct a water image and/or a fat image, i.e., an MR image showing only signal contributions from water or fat, respectively.

As mentioned above, signal contributions from flowing water molecules accumulate phase offsets in the bipolar acquisition which can lead to leakage and swapping artifacts which means that signal contributions from water are wrongly allocated to the fat image and vice versa.

The invention proposes to detect these artifacts by extrapolating the phase of the first single echo image to a zero echo time such that a 'virtual' single echo image at an echo time of zero is computed. Local variations in the phase of this zero echo time image are searched for. It is the insight of the invention that these local phase variations can be readily identified as flow-induced phase offsets. The corresponding flow-induced artifacts are then suppressed by appropriately adjusting the phase of the first single echo image.

Finally, a water image and/or a fat image are reconstructed using a conventional two-point Dixon algorithm using the phase-corrected first single echo image and the second single echo image.

The invention thus proposes a detection and correction of flow-induced leakage and swapping artifacts in bipolar dual-echo Dixon imaging by pure post-processing. The acquisition remains unchanged. Undesirable signal swaps and misallocations due to flow are significantly reduced by the method of the invention.

In a preferred embodiment of the invention, phase errors in the single echo images induced by the receive chain (RF coils, amplifiers, filters etc.) of the used MR device and/or by the gradient switching (eddy currents) during acquisition of the echo signals are corrected for prior to computing the zero echo time image. Such phase errors can be determined and eliminated using well-known calibration techniques.

Furthermore, phase errors induced by the transmit chain (RF pulses, amplifiers, coils etc.) can be assumed to have a smooth spatial variation and may thus be removed by high-pass spatial filtering of the phase of the zero echo time image.

According to a simple and straight-forward implementation of the method of the invention, the flow-induced phase errors may be identified in the zero echo time image by voxel-wise comparison of the (absolute) phase of the zero echo time image with a predetermined threshold value. Phase values exceeding the threshold are regarded as flow-induced artifacts and are corrected accordingly.

In an alternative implementation, the flow-induced phase errors are identified by comparison of the phase differences between adjacent voxels of the zero echo time image with a predetermined threshold value. In this embodiment, local variations in the phase of the zero echo time image are detected. In other words, not the absolute phase of the zero echo time image is looked at, but the phase differences between adjacent voxels of the zero echo time image are compared with a threshold value to identify the phase errors.

In a more complex implementation, the flow-induced phase errors can be identified by searching for sets of voxels aligned with the direction of the bipolar readout magnetic field gradients applied during acquisition of the echo signals. Flow-induced phase errors are likely to occur in voxels located in or containing blood vessels of the examined patient. No relevant phase errors are to be expected from static tissue in which no flow occurs. Corresponding to the typical geometrical shape of blood vessels, phase errors occurring in sets of voxels aligned with the bipolar readout magnetic field gradients are a strong indication of flow artifacts which can be used to identify the flow-induced phase errors in the zero echo time image according to the invention.

In a yet more complex implementation, the pixel-wise amplitude of the zero echo time image is also considered for the identification of the flow-induced phase errors. In this way, only phase errors within image regions attributed to blood vessels are considered. The respective voxels can be identified as belonging to blood vessels by methods known from MR angiography.

In a further preferred embodiment of the method of the invention, the phase correction of the first single echo image is performed by scaling the phase errors identified and estimated in the zero echo time image appropriately, taking the first and the second echo time value into account, and subtracting them from the phase of the first single echo image.

The method of the invention described thus far can be carried out by means of a MR device including at least one main magnet coil for generating an essentially uniform, static magnetic field $B_0$ within an examination volume, a number of gradient coils for generating switched magnetic field gradients in different spatial directions within the examination volume, at least one body RF coil for generating RF pulses within the examination volume and/or for receiving MR signals from a body of a patient positioned in the examination volume, a control unit for controlling the temporal succession of RF pulses and switched magnetic field gradients, and a reconstruction unit for reconstructing MR images from the received MR signals. The method of the invention can be implemented by a corresponding programming of the reconstruction unit and/or the control unit of the MR device.

The method of the invention can be advantageously carried out on most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention.

In the drawings.

DETAILED DESCRIPTION OF THE EMBODIMENTS

Figure 1:
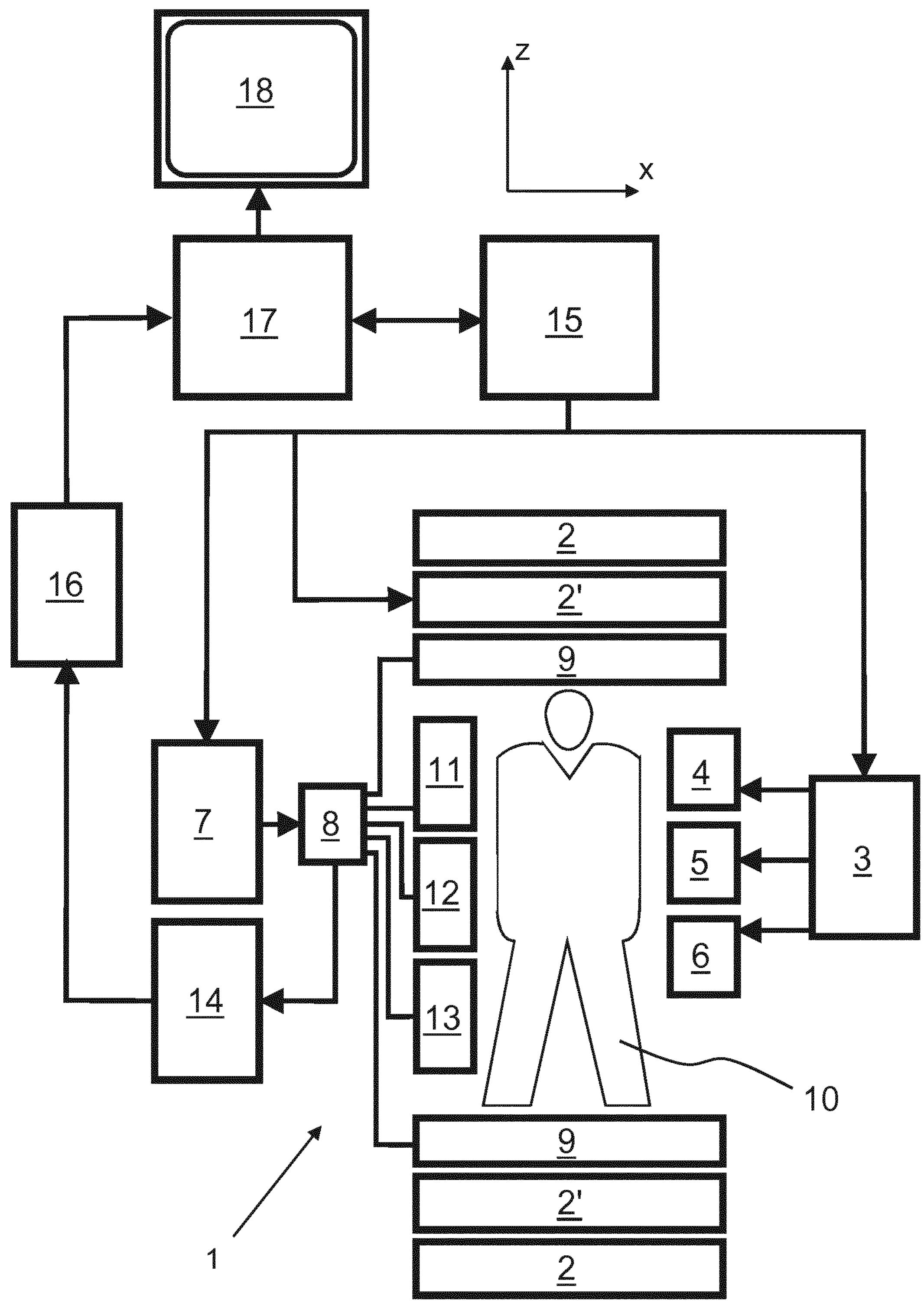
FIG. 1 shows a MR device for carrying out the method of the invention.

With reference to FIG. 1, a MR device 1 is shown as a block diagram. The device comprises superconducting or resistive main magnet coils 2 such that a substantially uniform, temporally constant main magnetic field $B_0$ is created along a z-axis through an examination volume. The device further comprises a set of ($1^{st}$, $2^{nd}$ and—where applicable—$3^{rd}$ order) shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send/receive switch 8, to a body RF coil 9 to transmit RF pulses into the examination volume. A typical MR imaging sequence is composed of a packet of RF pulse segments of short duration which, together with any applied magnetic field gradients, achieve a selected manipulation of nuclear magnetic resonance. The RF pulses are used to saturate resonance, excite resonance, invert magnetization, refocus resonance, or manipulate resonance and select a portion of a body 10 positioned in the examination volume. The MR signals are also picked up by the body RF coil 9.

For generation of MR images of limited regions of the body 10, a set of local array RF coils 11, 12, 13 are placed contiguous to the region selected for imaging. The array coils 11, 12, 13 can be used to receive MR signals induced by RF transmissions via the body RF coil.

The resultant MR signals are picked up by the body RF coil 9 and/or by the array RF coils 11, 12, 13 and demodulated by a receiver 14 preferably including a preamplifier (not shown). The receiver 14 is connected to the RF coils 9, 11, 12 and 13 via the send/receive switch 8.

A host computer 15 controls the shimming coils 2' as well as the gradient pulse amplifier 3 and the transmitter 7 to generate the imaging sequences of the invention. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data are reconstructed into an image representation by a reconstruction processor 17 which applies a Fourier transform or other appropriate reconstruction algorithms, such as SENSE. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

The host computer 15 and the reconstruction processor 17 are programmed to execute the method of the invention as described above and in the following.

Figure 2:
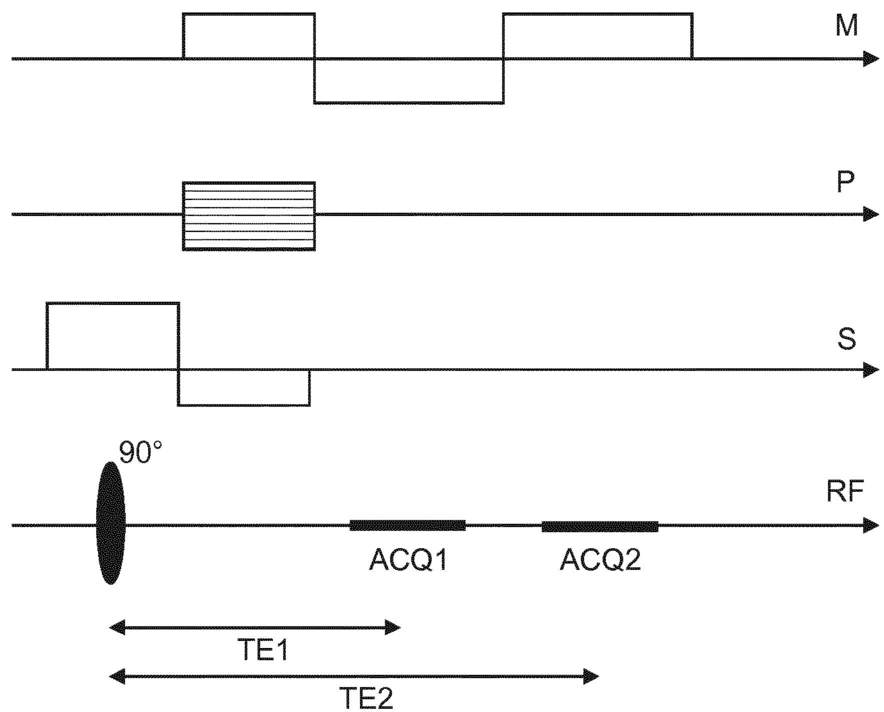
FIG. 2 shows a schematic (simplified) pulse sequence diagram of a Dixon imaging sequence using bipolar readout magnetic field gradients according to the invention.

In FIG. 2, a schematic pulse sequence diagram of a Dixon imaging sequence using bipolar readout magnetic field gradients according to the invention is depicted. The diagram shows switched magnetic field gradients in the frequency-encoding direction (M), the phase-encoding direction (P) and the slice-selection direction (S). Moreover, the diagram shows an RF excitation pulse as well as the time intervals during which echo signals are acquired, designated by ACQ1 and ACQ2. The diagram covers the acquisition of one pair of echo signals. A number of such pairs of echo signals is acquired by multiple repetitions of the depicted sequence using different phase encodings (P) to completely cover the required region of k-space. Each pair of echo signals is acquired using a corresponding pair of readout magnetic field gradients (M) having opposed polarities. The timing and amplitudes of the bipolar readout gradients are chosen to shift the acquisition windows ACQ1, ACQ2 of the echo signals such that different echo times TE1 (first echo time) and TE2 (second echo time) and correspondingly different phase offsets of the signal contributions from water protons and fat protons are provided. The Dixon-type separation of these signal contributions is based on these phase offsets in the final step of reconstruction of a water and/or a fat image.

According to the invention, single echo images are reconstructed from the acquired echo signals. A first single echo image attributed to the first echo time TE1 is reconstructed from the first echo signals, and a second single echo image attributed to the second echo time TE2 is reconstructed from the second echo signals.

It is assumed that the phase in each voxel of the two single echo images acquired at echo times TE1 and TE2 is the sum of the following different phase contributions:

RF excitation-related phase,
Receive chain-induced phase,
Chemical shift-induced phase,
Main field inhomogeneity-induced phase,
Gradient switching-induced phase,
Flow-induced phase.

At first, the phase contributions from the receive chain and the gradient switching are removed based on a suitable system calibration.

Figure 3:
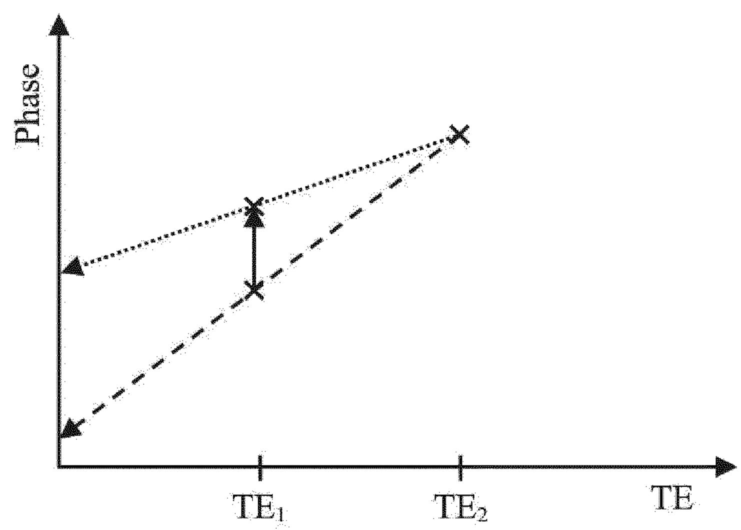
FIG. 3 shows a diagram illustrating the phase extrapolation for computing the zero echo time image according to the invention.

In a second step, the chemical shift-induced phase and the main field inhomogeneity-induced phase are eliminated according to the invention by extrapolating the phase of the first single echo image to an echo time of zero (TE=0 ms) to obtain a 'virtual' zero echo time image. For this purpose, the phase difference between the two single echo images is scaled by the ratio TE1/(TE2−TE1) and subtracted from the phase of the first single echo image. FIG. 3 illustrates the phase in a single voxel of the two single echo images at TE1 and TE2, once without flow (lower crosses) and once with flow (upper crosses). Flow selectively affects the phase at TE1, typically leading to a significantly larger or different (absolute) phase at TE=0 ms. Depending on TE1 and TE2, an unwrapping of the phase difference between the two single echo images may be advantageous. Additionally, a comparison of the amplitude of the first and the second single echo images allows identifying voxels which contain substantial amounts of both water and fat. Especially for these, a simple scaling of the phase difference between the two single echo images may be too inaccurate. A Dixon water/fat separation may be applied instead for these voxels to improve the extrapolation of the phase to an echo time of zero.

The phase of the computed zero echo time image then reflects the phase contributions from the RF excitation and the flow only.

The phase contribution from the RF excitation is a static contribution at TE=0 ms, which primarily depends on the Larmor frequency $f_0$, the radiofrequency magnetic field $B_1$, as well as the permittivity $\varepsilon$ and the electric conductivity $\sigma$ of the imaged tissues. Assuming spatial smoothness, this phase contribution can be removed by filtering, e.g. by applying an appropriate spatial high pass filter. Alternatively or additionally, a suitable system calibration, e.g. to measure $B_1$, can be performed to simulate this contribution, e.g. based on a patient model. The RF excitation-related phase can also be measured separately, using e.g. any of the known methods developed for electric properties tomography.

Following the model employed by Rahimi et al (Magn. Reson. Med., 73:1926-1931, 2015), the flow-induced phase errors affect only the first single echo image, because the first moment of the bipolar readout magnetic field gradients vanishes only at TE2, but not at TE1. For flow with constant velocity along the readout direction, this leads to an increase or decrease of the phase difference between the two single echo images and thus to an offset in the phase of the 'virtual' zero echo time image (at TE=0 ms) in the concerned blood vessel relative to adjacent, static tissues (see FIG. 3).

A local, substantial increase or decrease of the phase difference between the two single echo images can cause leakage and swapping artifacts in the Dixon water/fat separation since the estimation of the main field inhomogeneity being part of the Dixon algorithm is perturbed and the assumption of spatial smoothness of the main field inhomogeneity is violated.

To suppress such leakage and swapping artifacts, local variations in the phase of the zero echo time image are detected to identify the flow-induced phase errors. After the corrections described above, a simple implementation applies a threshold to the (absolute) phase at TE=0 ms only. A somewhat more complex implementation searches for sets of voxels aligned with the readout direction, in which the (absolute) phase exceeds the threshold. In particular in contrast-enhanced imaging, it also considers the signal amplitude in the voxels of the two single echo images to preferably select sets of voxels within blood vessels only.

Finally, the phase in the selected voxels is adjusted in the first single echo image, such that the phase in the respective voxels in the zero echo time image approximately matches the phase in adjacent, non-selected voxels in the zero echo time image.

After this phase correction of the first single echo image the Dixon water/fat separation is performed using the phase-corrected first single echo image and the (original) second single echo image to reconstruct a water image and/or a fat image.

The invention claimed is:

1. A method of magnetic resonance (MR) imaging of an object placed in an examination volume of a MR device, the method comprising:

subjecting the object to an imaging sequence, which comprises at least one excitation RF pulse and switched magnetic field gradients, wherein two echo signals, a first echo signal and a second echo signal, are generated at different echo times (TE1, TE2), acquiring the echo signals from the object using bipolar readout magnetic field gradients, reconstructing a first single echo image from the first echo signals and a second single echo image from the second echo signals, computing a zero echo time phase image by extrapolating the phase of the first single echo image at each voxel position to a zero echo time using the phase difference between the first and the second single echo image at the respective voxel position, identifying and estimating flow-induced phase errors from local phase variations in the zero echo time phase-image, correcting the phase of the first single echo image according to the estimated flow-induced phase errors, and reconstructing a water image and/or a fat image from the echo signals, wherein contributions from water and fat to the echo signals are separated using the phase-corrected first single echo image and the second single echo image.

2. The method of claim 1, wherein phase errors in the single echo images induced by the receive chain of the used MR device and/or by the gradient switching during acquisition of the echo signals are corrected for prior to computing the zero echo time phase image.

3. The method of claim 1, wherein phase errors induced by the excitation RF pulse are removed by high-pass spatial filtering of the zero echo time phase image.

4. The method of claim 1, wherein the flow-induced phase errors are identified in the zero echo time phase image by voxel-wise comparison of the phase of the zero echo time phase image with a predetermined threshold value.

5. The method of claim 1, wherein the flow-induced phase errors are identified by comparison of the phase differences between adjacent voxels of the zero echo time phase image with a predetermined threshold value.

6. The method of claim 4, wherein the flow-induced phase errors are identified in the zero echo time phase image by searching for sets of voxels aligned with the direction of the bipolar readout magnetic field gradients applied during acquisition of the echo signals.

7. The method of claim 4, wherein a zero echo time image's amplitude is also considered for the identification of the flow-induced phase errors.

8. The method of claim 4, wherein only phase errors within image regions attributed to blood vessels are considered.

9. The method of claim 1, wherein the phase correction of the first single echo image is performed by scaling the phase errors identified and estimated in the zero echo time phase image and subtracting them from the phase of the first single echo image.

10. The method of claim 1, wherein the water image and/or the fat image are reconstructed using a two-point Dixon technique.

11. A magnetic resonance (MR) device comprising at least one main magnet coil for generating a uniform, static magnetic field $B^0$ within an examination volume, a number of gradient coils for generating switched magnetic field gradients in different spatial directions within the examination volume, at least one RF coil for generating RF pulses within the examination volume and/or for receiving MR signals from an object positioned in the examination volume, a control unit for controlling the temporal succession of RF pulses and switched magnetic field gradients, and a reconstruction unit for reconstructing MR images from the received MR signals, wherein the MR device is configured to: subject the object to an imaging sequence, which comprises at least one excitation RF pulse and switched magnetic field gradients, wherein two echo signals, a first echo signal and a second echo signal, are generated at different echo times (TE1, TE2), acquire the echo signals from the object using bipolar readout magnetic field gradients, reconstruct a first single echo image from the first echo signals and a second single echo image from the second echo signals, compute a zero echo time phase image by extrapolating the phase of the first single echo image at each voxel position to a zero echo time using the phase difference between the first and the second single echo image at the respective voxel position, identify and estimating flow-induced phase errors from local phase variations in the zero echo time phase-image, correct the phase of the first single echo image according to the estimated flow-induced phase errors, and reconstruct a water image and/or a fat image from the echo signals, wherein contributions from water and fat to the echo signals are separated using the phase-corrected first single echo image and the second single echo image.

12. A computer program comprising:

executable instructions stored on a non-transitory computer readable storage medium, which when executed by a magnetic resonance (MR) device, causes the MR device to subject the object to an imaging sequence, which comprises at least one excitation RF pulse and switched magnetic field gradients, wherein two echo signals, a first echo signal and a second echo signal, are generated at different echo times (TEL TE2), acquire the echo signals from the object using bipolar readout magnetic field gradients, reconstruct a first single echo image from the first echo signals and a second single echo image from the second echo signals, compute a zero echo time phase image by extrapolating the phase of the first single echo image at each voxel position to a zero echo time using the phase difference between the first and the second single echo image at the respective voxel position, identify and estimating flow-induced phase errors from local phase variations in the zero echo time phase-image, correct the phase of the first single echo image according to the estimated flow-induced phase errors, and reconstruct a water image and/or a fat image from the echo signals, wherein contributions from water and fat to the echo signals are separated using the phase-corrected first single echo image and the second single echo image.

* * * * *